United States Patent [19]

Schally et al.

[11] Patent Number: 5,198,533

[45] Date of Patent: * Mar. 30, 1993

[54] LHRH ANTAGONISTS

[75] Inventors: Andrew V. Schally, Metarie; Sandor Bajusz, New Orleans, La.

[73] Assignee: The Administrators of the Tulane Educational Fund, New Orleans, La.

[*] Notice: The portion of the term of this patent subsequent to Jan. 24, 2006 has been disclaimed.

[21] Appl. No.: 197,153

[22] Filed: May 23, 1988

Related U.S. Application Data

[63] Continuation-in-part of Ser. No. 74,126, Jul. 17, 1987, abandoned.

[51] Int. Cl.$^5$ .............................................. C07K 7/20
[52] U.S. Cl. .................................... 530/313; 530/328; 930/110; 930/120; 930/DIG. 803; 930/DIG. 801; 930/DIG. 800
[58] Field of Search .................. 530/313, 328; 514/15, 514/800; 930/110, 120, DIG. 803

[56] References Cited

U.S. PATENT DOCUMENTS

| | | | |
|---|---|---|---|
| 3,250,759 | 5/1966 | Bodanszky et al. | 530/328 |
| 4,800,191 | 1/1989 | Schally et al. | 530/313 |

FOREIGN PATENT DOCUMENTS

| | | |
|---|---|---|
| 0081877 | 6/1983 | European Pat. Off. |
| 0097031 | 12/1983 | European Pat. Off. |
| 0145032 | 6/1985 | European Pat. Off. |
| 0175506 | 3/1986 | European Pat. Off. |
| 0182262 | 5/1986 | European Pat. Off. |
| 0192492 | 8/1986 | European Pat. Off. |
| 0199302 | 10/1986 | European Pat. Off. |

OTHER PUBLICATIONS

Ljunggvist et al, Biochem. & Biophys. Res. Com. pp. 849–856, vol. 148, No. 2, 1987.
Dutta et al, J. Med. Chem., vol. 21, pp. 1018–1024, 1978.
Bajasz et al, PNAS, vol. 85, pp. 1637–1641, 1988.
M. Karten and J. E. Rivier, Endocrine Reviews, 7, 44–66 (1986).
D. H. Coy, et al. Peptides: Structure and Biological Function, 775–779, (1979).
J. L. Pineda, et al., Journal of Clin. Endocrinology and Metabolism 421–422 (1980).
Coy, et al., vol. 110, No. 4, Endocrinology 1445–1447 (1982).
Schmidt, et al., Contraception vol. 29, No. 3, (Mar. 1984).
Morgan, et al., Int. Archs Allergy appl. Immun. 80: 70–75 (1986).
Vickery, et al, LHRH and Its Analogs, MTP Press, Ltd., 11–22 (1984).
Activities of Sntagonists of the Luteinizing Hormone Releasing Hormone with Emphasis on Positions 1, 5 and 6, etc. Folkers, et al., Biomed Research Chemical Abstracts, vol. 82, (1975), 73465h, p. 488.
Chemical Abstracts, vol. 110 (1989), 110:186130k, p. 94.

*Primary Examiner*—Merrell C. Cashion, Jr.
*Assistant Examiner*—T. D. Wessendof
*Attorney, Agent, or Firm*—Omri M. Behr; Matthew J. McDonald

[57] ABSTRACT

The present invention deals with LHRH antagonists which possess improved water solubility and while having the high antagonist potency of the basic peptides, are free of the edematogenic effects. These compounds are highly potent in inhibiting the release of gonadotropins from the pituitary gland in mammals, including humans.

The compounds of this invention are represented by the formula

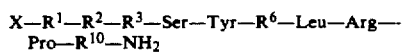

$$X—R^1—R^2—R^3—Ser—Tyr—R^6—Leu—Arg—Pro—R^{10}—NH_2$$

wherein
X is an acyl group derived from straight or branched chain aliphatic or alicyclic carboxylic acids having from 1 to 7 carbon atoms, or $H_2N—CO$,
$R^1$ is D— or L—Pro, D— or L—$\Delta^3$—Pro, D—Phe, D—Phe(4—H1), D—Ser, D—Thr, D—Ala, D—Nal(1) or D—Nal (2),
$R^2$ is D—Phe or D—Phe(4—Cl)
$R^3$ is D—Trp, D—Phe, D—Pal(3), D—Nal(1) or D—Nal(2),
$R^6$ is D—Cit, D—Hci, D—Cit(Q) or D—Hci(Q) and
$R^{10}$ is Gly or D—Ala where Q is lower alkyl of 1–3 carbon atoms and H1 is fluoro, chloro or bromo, and the pharmaceutically acceptable acid addition salts thereof and methods of use pertaining to these compounds.

2 Claims, No Drawings

LHRH ANTAGONISTS

This invention was made with Government support under Grant Nos. CA40003 and 40004, awarded by the N.C.I. (NIH). The U.S. Government has certain rights in this application.

RELATED APPLICATIONS

This application is a continuation-in-part of copending application, Ser. No. 074,126, filed Jul. 17, 1987, now abandoned.

BACKGROUND OF THE INVENTION

The present invention relates to novel peptides which inhibit the release of gonadotropins by the pituitary gland in mammals without inducing edematous reactions. More specifically, the present invention relates to analogs of the luteinizing hormone releasing hormone (LHRH), which has the structure:

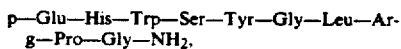

salts thereof, and to pharmaceutical compositions and methods of use pertaining to these analogs.

DISCUSSION OF THE PRIOR ART

For more than 15 years, investigators have been searching for selective, potent antagonists of the LHRH decapeptide (M. Karten and J. E. Rivier, Endocrine Reviews, 7, 44–66 (1986)). The high degree of interest in such antagonists is due to their usefulness in the fields of endocrinology, gynecology, contraception and cancer. A large number of compounds have been prepared as potential LHRH antagonists. The most interesting antagonists to date have been compounds whose structure is a modification of the structure of LHRH.

The first series of potent antagonists was obtained by introduction of aromatic amino acid residues into positions 1, 2, 3 and 6, or, 2, 3, and 6. The compounds are expressed as LHRH modified by replacement of the original amino acid residues by others at the position indicated by the superscript numbers. The known antagonists include:

[Ac-D-Phe(4-Cl)[1,2], D-Trp[3,6]] LHRH (D. H Coy, et al., In: Gross, E. and Meienhofer, J. (eds) Peptides, Proceedings of the 6th. American Peptide Symposium, pp. 775–779, Pierce Chem. Co., Rockville Ill., 1979);

[Ac-Pro[1], D-Phe(4-Cl)[2] D-Nal(2)[3,6]] LHRH (U.S. Pat. No. 4,419,347); and [Ac-Δ[3]Pro[1],D-Phe(4-Cl)[2],D-Trp[3,6]]LHRH (J. L. Pineda, et al., J. Clin. Endocrinol. Metab. 56, 420, 1983).

Later, in order to increase the water solubility of antagonists, basic amino acids, such as D-Arg, were introduced into position 6. For instance, [Ac-D-Phe(4-Cl)[1,2], D-Trp[3], D-Arg[6], D-Ala[10]]LHRH (ORG-30276) (D. H. Coy, et al., Endocrinology, 100, 1445, 1982); and [Ac-D-Nal(2)[1], D-Phe(4-F)[2], D-Trp[3], D-Arg[6]]LHRH (ORF-18260) (J. E. Rivier, et al., In: Vickery B. H., Nestor, Jr. J. J., Hafez, E.S.E. (eds), LHRH and Its Analogs, pp. 11–22, MTP Press, Lancaster, UK, 1984).

These analogs not only possessed the expected improved water solubility but also showed increased antagonistic activity. However, these highly potent, hydrophilic analogs containing D-Arg and other basic side chains at position 6 proved to produce transient edema of the face and extremities when administered subcutaneously in rats at 1.25 or 1.5 mg/kg (F. Schmidt, et al., Contraception, 29, 283, 1984; J. E. Morgan, et al., Int. Archs. Allergy Appl. Immun. 80, 70, (1986). Since the occurrence of edematogenic effects after administration of these antagonists to rats cast doubts on their safety for the use in humans and delayed the introduction of these drugs for clinical use, it is desirable to provide antagonistic peptides which are free of these side effects.

SUMMARY OF THE INVENTION

The present invention deals with LHRH antagonists which possess an improved water solubility and high antagonist potency of the basic peptides, and are free of the edematogenic effects. These compounds are highly potent in inhibiting the release of gonadotropins from the pituitary gland in mammals, including humans.

The compounds of this invention are represented by formula I

wherein
X is an acyl group derived from straight or branched chain aliphatic or alicyclic carboxylic acids having from 1 to 7 carbon atoms, or a carbamyl ($H_2N-CO$) group.
$R^1$ is D— or L—Pro, D— or L—$\Delta^3$—Pro, D—Phe, D—Phe(4—Hl), D—Ser,
D—Thr, D—Ala, D—Nal(1) or D—Nal(2),
$R^2$ is D—Phe or D—Phe(4—Cl)
$R^3$ is D—Trp, D—Phe, D—Pal(3), D—Nal(1) or D—Nal(2),
$R^6$ is D—Cit, D—Hci, D—Cit(Q) or D—Hci(Q) and
$R^{10}$ is Gly or D—Ala
where Q is lower alkyl of 1–3 carbon atoms and Hl is fluoro, chloro or bromo, and the pharmaceutically acceptable acid addition salts thereof.

The compounds of Formula I are synthesized by any suitable method. For example, exclusively solid-phase technique, partial solid-phase technique or by classical solution couplings Preferably, the compounds of Formula I are prepared by a known solid-phase technique. Such method provides intermediate peptides and/or intermediate peptide-resins of Formula II.

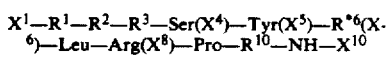

wherein
$X^1$ is an acyl group derived from straight and branched chain aliphatic or alicyclic carboxylic acids having from 1 to 7 carbon atoms, t-Boc, carbamyl or hydrogen,
$X^4$ is hydrogen or a protecting group for the Ser hydroxyl group,
$X^5$ is hydrogen or a protecting group for the Tyr phenolic hydroxyl group,
$X^6$ is hydrogen or a protecting group for the Lys or Orn side chain amino group,
$X^8$ is hydrogen or a protecting group for the Arg guanidino group,
$X^{10}$ is hydrogen or a resin support containing benzhydryl or methylbenzhydryl groups
$R^1$ is D— or L—Pro, D— or L—$\Delta^3$—Pro, D—Phe, D—Phe(4—Hl), D—Ser, D—Thr, D—Ala, D—Nal(1) or D—Nal(2), $R^2$ is D—Phe or D—Phe(4—Cl),
$R^3$ is D—Trp, D—Phe, D—Pal(3), D—Nal(1) or D—Nal(2),
$R^{*6}$ is D—Lys or D—Orn, D—Cit and D—Hci
and $R^{10}$ is Gly or D—Ala
where Hl is fluoro, chloro or bromo.

One process comprises reacting a peptide of Formula II wherein $R^{*6}$ is D-Lys or D-Orn and $X^6$ is hydrogen, with a source of cyanate to yield a peptide of Formula III:

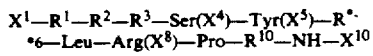

III wherein $X^1$, $R^1$, $R^2$, $R^3$, $X^4$, $X^5$, $X^8$, $R^{10}$ and $X^{10}$ are as defined above, and $R^{**6}$ is Cit or Hci. Suitably, the reaction is carried out when $X^1$ is acyl and all other X moieties are hydrogen. Suitable cyanate sources are alkali metal cyanates, e.g., potassium cyanate, or an N-alkyl isocyanate, e.g., N-ethyl-isocyanate. The peptide of Formula II are preferably synthesized by a known solid phase technique.

Alternatively and preferably, peptides of Formula I wherein X is an acyl or carbamyl group, are directly obtained by cleavage and deprotection of intermediate peptide-resins of Formula II wherein $X^1$ is an acyl or carbamyl group and $R^{*6}$ is D-Cit or D-Hci. Peptides of Formula I wherein X is carbamyl ($H_2N$—CO) group are also obtained from peptide-resins of Formula II wherein $X^1$ is hydrogen or Boc by cleavage and deprotection followed by carbamoylation.

A gonadotropin antagonizing pharmaceutical composition is provided by admixing the compound of Formula I with a pharmaceutically acceptable carrier including microcapsules (microspheres) for delayed delivery.

There is also provided a method for relieving complications resulting from the physiological availability of amounts of pituitary gonadotropins in a mammal, in excess of the desired amount, which involves administering to the mammal a gonadotropin antagonizing dose of the compound of Formula I.

DESCRIPTION OF THE PREFERRED EMBODIMENTS

The nomenclature used to define the peptides is that specified by the IUPAC-IUB Commission on Biochemical Nomenclature (*European J. Biochem.*, 1984, 138, 9-37), wherein in accordance with conventional representation the amino groups at the N-terminus appears to the left and the carboxyl group at the C-terminus to the right. By natural amino acid is meant one of the common, naturally occurring amino acids found in proteins comprising Gly, Ala, Val, Leu, Ile, Ser, Thr, Lys, Arg, Asp, Asn, Glu, Gln, Cys, Met, Phe, Tyr, Pro, Trp and His. The abbreviations for the individual amino acid residues are based on the trivial name of the amino acid and are Ala, alanine; Arg, arginine; Cit, citrulline; Gly, glycine; Hci, homocitrulline; Leu, leucine; Lys, lysine; Pal(3), 3-(3-pyridyl)alanine; Nal(1), Nal(2), 3-(1-naphtyl)alinine, 3-(2-naphthyl)alanine; Orn, ornithine; Phe, phenylalanine; Phe(4-Cl), 4-chlorophenylalanine; Phe (4-F), 4-fluorophenylalanine; Pro, proline; Ser, serine; Trp, tryptophan and Tyr, tyrosine. All amino acids described herein are of the L-series unless stated otherwise, e.g., D-Trp represents D-tryptophan and D-Nal(2) represents 3-(2-naphthyl)-D-alanine.

Other abbreviations used are:

| | |
|---|---|
| AcOH | acetic acid |
| AcOEt | ethyl acetate |
| Ac₂O | acetic anhydride |
| Boc- | tert.butyloxycarbonyl- |
| DIC | diisopropylcarbodiimide |
| DIEA | diisopropylethylamine |
| DMF | dimethylformamide |
| HOBt | 1-hydroxybenzenetriazole hydrate |
| HPLC | high performance liquid chromatography |
| MeOH | methyl alcohol |
| TEA | triethylamine |
| DCC | dicyclohexylcarbodiimide |
| MeCN | acetonitrile |
| IpOH | isopropanol |
| Z(2-Cl) | 2-chloro-benzyloxycarbonyl |
| DCB | 2,6-dichlorobenzyl |
| Tos | p-toluenesulfonyl |
| TFA | trifluoroacetic acid |
| Z | benzyloxycarbonyl |

Especially preferred are LHRH analogs of Formula I wherein:
$X^1$ is acetyl or carbamyl
$R^1$ is Pro, D—Phe, D—Phe(4—Cl) or D—Nal(2),
$R^2$ is D—Phe(4—Cl) or D—Phe(4—F),
$R^3$ is D—Trp or D—Pal(3)
$R^6$ is D—Cit or D—Hci, and
$R^{10}$ is D—Ala.

The peptides are synthesized by a suitable method, such as by exclusively solid-phase techniques, by partial solid-phase techniques, by fragment condensation or by classical solution phase synthesis (See M. Bodanszky, "Principles of Peptide Synthesis", Springer-Verlag, 1984).

For example, the techniques of exclusively solid-phase synthesis are set forth in the textbook "Solid Phase Peptide Synthesis", J. M. Stewart and J. D. Young, Pierce Chem. Company, Rockford, Ill., 1984 (2nd. ed.), G. Barany and R. B. Merrifield, "The Peptides", Ch. 1, 1-285, pp. 1979, Academic Press, Inc.

Classical solution synthesis is described in detail in the treatise "Methoden der Organischen Chemie (Houben-Weyl): Synthese von Peptiden", E. Wunsch (editor) (1974) Georg Thieme Verlag, Stuttgart, W. Germany.

Common to such synthesis is the protection of the reactive side chain functional groups of the various amino acid moieties with suitable protecting groups which will prevent a chemical reaction from occurring at that site until the group is ultimately removed Usually also common is the protection of an alpha-amino group on an amino acid or a fragment while that entity reacts at the carboxyl group, followed by the selective removal of the alpha-amino protecting groups to allow subsequent reaction to take place at that location Accordingly, it is common that, as a step in the synthesis, an intermediate compound is produced which includes each of the amino acid residues located in its desired sequence in the peptide chain with side-chain protecting groups linked to the appropriate residues.

In Formula II:
$R^1$, $R^2$, and $R^3$ are as defined hereinabove,
$X^1$ is hydrogen or an acyl group derived from straight or branched chain aliphatic or alicyclic carboxylic acids having from 1 to 7 carbon atoms, or an alpha-amino protecting group. The alpha-amino protecting groups contemplated by $X^1$ are those well known to be useful in the art of step-wise synthesis of polypeptides. Among the classes of alpha-amino protecting groups which may be employed as $X^1$ may be mentioned fluoroenylmethyloxycarbonyl (Fmoc) or t-butyloxycarbonyl (Boc).

$X^4$ may be a suitable protecting group for the hydroxyl group of Ser such as benzyl (Bzl), and 2,6-dichloro-benzyl (DCB). The preferred protecting group is Bzl.

$X^5$ may be a suitable protecting group for the phenolic hydroxyl group of Tyr, such as Bzl, 2-Br-Z and 2,6-dichloro-benzyl (DCB). The preferred protecting group is DCB.

$X^6$ is a suitable protecting group for the side chain amino group of Lys or Orn. Illustrative of suitable side chain amino protecting groups are benzyloxycarbonyl (Z), and 2-chloro-benzyloxycarbonyl ((Z-(2-Cl)).

$X^8$ is a suitable protecting group for the guanidino group of Arg, such as nitro, Tos, methyl-(t-butyl benzene)-sulfonyl, 4-methoxy-2,3,6-trimethylbenzenesulfonyl; Tos is the preferred group.

$X^{10}$ is an amide protecting benzhydryl or methylbenzhydryl group incorporated into resin support; for the synthesis of peptide amides 98% styrene-2% divinylbenzene copolymers containing benzhydryl amine or methylbenzhydryl amine groups are preferred.

The selection of a side chain amino protecting group is not critical except that generally one is chosen which is not removed during deprotection of the alpha-amino groups during the synthesis.

The peptides of Formula I may be from intermediate peptide-resins of Formula II by procedures known in the art. The solid phase systhesis of intermediate peptide-resins of Formula II is essentially carried out as described by Merrifield, J. Am. Chem. Soc., 85, p. 2149 (1963). Solid phase synthesis is commenced from the C-terminal end of the peptide by coupling a protected amino acid to a suitable resin Such a starting material can be prepared by attaching -amino protected Gly or D-Ala by an amide bond to a benzylhydrilamine resin. Such resin supports are commercially available and generally used when the desired polypeptide being synthesized has an carboxamide at the C-terminal.

The selection of an appropriate coupling reagent is within the skill of the art. Particularly suitable as a coupling reagent is N,N'-diisopropyl carbodiimide (DIC).

Each protected amino acid or amino acid sequence is introduced into the solid phase reactor in about a two-three fold excess, and the coupling may be carried out in a medium of DMF:$CH_2Cl_2$ (1:1) or in $CH_2Cl_2$ alone. In cases where incomplete coupling occurs, the coupling procedure is repeated before removal of the alpha-amino protecting group prior to the coupling of the next amino acid. The success of the coupling reaction at each stage of the synthesis, is preferably monitored by the ninhydrin reaction, as described by E. Kaiser, et al., Anal. Biochem., 34, 595 (1970).

After the desired amino acid sequence of intermediates B has been completed, the terminal Boc group is removed and if desired, N-terminal acylation carried out using the appropriate acyl anhydride or acid chloride in 50-fold excess in a halogenated hydrocarbon solvent; suitably, acetic anhydride in methylene chloride for 30 minutes. The intermediate peptide can be removed from the resin support by treatment with a reagent such as liquid hydrogen fluoride, which not only cleaves the peptide from the resin but also cleaves all remaining side chain protecting groups $X^4$, $X^5$, $X^8$, $X^{10}$ and, if present, $X^6$.

When using hydrogen fluoride for cleaving, anisole or m-cresol, and, if desired, methylethyl sulfide are included as scavengers in the reaction vessel.

Peptides of Formula II wherein $R^{*6}$ is D-Lys or D-Orn and $X^6$ is hydrogen, are converted into peptides of Formula I by treatment with cyanate, suitably an alkali metal cyanate, preferably potassium cyanate, or an N-alkylisocyanate, for instance, N-ethylisocyanate, in DMF or aqueous DMF. The latter reaction, i.e., transformation of Orn/Lys-peptides into the corresponding Cit/Hci-peptides can be readily followed by HPLC using MeCN-aqueous TFA systems because of a characteristic 2.6±0.3 minutes increase of the retention times of Cit/Hci—and, for example, Cit(Et)/Hci(Et)-peptides relative to the corresponding Orn/Lys-peptides respectively.

When acylation is omitted, treatment of peptide-resins of Formula II with hydrogen fluoride yields decapeptides which have free omega-amino and/or alpha-amino groups and correspond to a Formula II where $X^1$, $X^4$, $X^5$, $X^8$, $X^{10}$, and, if present, $X^6$ are hydrogen. These free peptides are converted into peptides of Formula I wherein X is carbamyl by treatment with cyanate, suitably an alkali metal cyanate, preferably potassium cyanate. The latter reaction, i.e., transformation of $H_2N$ into $H_2N-CO-NH$ at the amino terminus of peptides and conversion of the Orn/Lys residues into the Cit/Hci residues, can be easily followed by HPLC using MeCN-aqueous TFA systems, because of a characteristic 2-3 min. increase of the retention times of carbamylated peptides, i.e., compounds with $H_2N-CO-NH-$ group, relative to their congeners with $H_2N$ group.

Alternatively and preferably, peptides of Formula I wherein X is an acyl or carbamyl group, are directly obtained by cleavage and deprotection of intermediate peptide-resins of Formula II, where $X^1$ is an acyl or carbamyl group and $R^{*6}$ is D-Cit or D-Hci.

Although an exclusively solid-phase synthesis and a partially solid-phase synthesis of compounds of Formula I are disclosed herein, the preparation of the compounds also can be realized by classical solution-phase methods.

The synthetic peptides prepared as described in the Examples are compared with two of the most potent LHRH antagonists reported recently, i.e., [Ac-D-Phe(4-Cl)[1,2], D-Trp[3], D-Arg[6], D-Ala[10]] LHRH (ORG-30276) (Coy, et al., Endocrinology, 100, 1445, 1982) and [Ac-D-Nal(2)[1], D-Phe(4-F)[2], D-Trp[3], D-Arg[6]] LHRH (ORF 18260) (Rivier, et al., In: Vickery, B. H., Nestor, Jr., J. J. Hafez, E. S. E. (eds.), LHRH and Its Analogs, pp. 11–22, MTP Press, Lancaster, UK, 1984), and are found to exert similarly high inhibitory activities both in vitro and in vivo, but, unlike to the control peptides, not to produce the in vivo edematous effects.

Hormonal activities in vitro are compared in superfused rat pituitary cell systems (S. Vigh and A. V. Schally, Peptides. 5 suppl. 1: 241–247, 1984) in which the effectiveness of LHRH (and other releasing hormones) can be accurately evaluated since the amount of LH (or other pituitary hormones) secreted into the effluent medium is not only proportional to the hormone-releasing potency of the peptide applied but also measurable readily by well-characterized radioimmunoassays.

To determine the potency of an LHRH antagonist, mixtures containing LHRH in a constant concentration (usually 1 nM) and the antagonist in varying concentrations are used for the superfusion in order to determine the molecular ratio of the antagonist to LHRH at which the action of LHRH is completely blocked. These ratios are about 5 for both peptides of the present invention and the control peptides when the rat pituitary cell system is preincubated with antagonists for 9 minutes.

In an antiovulatory in vivo assay (A. Corbin and C. W. Beattie; Endocr. Res. Commun. 2, 1-23, 1975; D. H. Coy, et al., Endocrinology, 100, 1445, 1982), the peptides of the present invention are also found to be about equipotent to the control antagonist, namely, 87.5-100% blockade of ovulation can be observed at a subcutaneous dose of 1-3 ug/rat for each peptide.

In the edematogenic test of Schmidt, et al. (Contraception, 29, 283-289, 1984), however, a marked difference can be found between the control peptides and the peptides of the present invention. The control administered subcutaneously in rats at doses of 1.25 or peptides produce edema of the face and extremities when 1.50 mg/kg. No such reaction can be observed with the peptides of the present invention when given at a subcutaneous dose of 1.5 mg/kg.

In the tests as run, the rats were assigned to three groups of five rats per group per compound tested. Comparison was made with a known prior art compound designated ORG 30276 namely (N-Ac-D-p-Cl-Phe$^{1,2}$,D-Trp$^3$, D-Arg$^6$,D-Ala$^{10}$)-LHRH. The groups were injected subcuntaneously once a day on two consecutive days with the LHRH antagonists at a dose level of 1.5 mg/kg. One control group was injected with diluent only. The rats were observed during five hours each day. Reactions of the rats were classified as follows: NR no apparent reaction, PR partial responders: edema of the nasal and paranasal area, FR full responders: facial edema with edematous extremities.

These results are summarized in Table 1 below.

TABLE 1

| LHRH | 1st Day | | | 2nd Day | | |
|---|---|---|---|---|---|---|
| Antagonist | NR | PR | FR | NR | PR | FR |
| ORG 30276 | 3 | 7 | 0 | 0 | 0 | 10 |
| Control | 9 | 0 | 0 | 9 | 0 | 0 |
| EX III | 8 | 0 | 0 | 8 | 0 | 0 |
| EX V | 9 | 0 | 0 | 8 | 1* | 0 |
| EX IV | 9 | 0 | 0 | 9 | 0 | 0 |
| EX I | 8 | 0 | 0 | 8 | 0 | 0 |
| EX XX | 9 | 0 | 0 | 8 | 1* | 0 |
| EX XXI | 9 | 0 | 0 | 9 | 0 | 0 |
| EX XXVI | 8 | 0 | 0 | 8 | 0 | 0 |
| EX XXVII | 9 | 0 | 0 | 9 | 0 | 0 |

*Very light edema of the face.

LHRH secretion in vitro at some reasonable concentration, although most are slightly less potent than the present standard in vitro; however, these peptides are much more potent in vivo.

This was shown by a test on histamine release in vitro from peritoneal mast cells carried out in accordance with the procedure of Morgan et al (Int. Archs. Allergy appl. Immun. 80, 70 1986).

Histamine Release In Vitro

In this test rats were anesthetized with ether and peritoneal exudate cell were harvested by washing with 12 ml. of mast cell medium (MCM) (150m M NaCl; 3.7m M KCl; 3.0m M Na$_2$HPO$_4$; 3.5m M KH$_2$PO$_4$, 0.98m M CaCl; 5.6m M dextrose; 0.1% bovine serum albumin; 0.1% gelatin and 10 units/ml heparin)[9]. Cells from 4 or 5 rats were pooled, centrifuged at 120 g, resuspended with MCM to a concentration of $0.5 \times 10^6$ ml and 1 ml was aliquoted into $12 \times 75$ mm polyethylene tubes. Tubes were equilibrated to 37° C. for 15 min and incubated alone (background histamine release), with 48/80 (positive control) (Sigma Chemicals, St. Louis, Mo.), or with appropriate concentrations (1 ng through 10 ug/ml) of LHRH antagonists for 60 min. The reaction was terminated by cooling the tubes to 4° C. Tubes were centrifuged; supernatants were recovered and stored at −20° C. until assayed for histamine. Assays were performed in duplicate. Total cell histamine was determined by boiling for 10 min. Histamine released in reponse to antagonist was expressed as a percentage of total release. That concentration that released 50% of total mast cell histamine (HRD$_{50}$ ug/ml) was determined for each antagonist. The results are summarized in FIG. 1.

All of the peptides are considered to be effective to prevent ovulation of female mammals at very low dosages. The peptides of the invention are often administered in the form of pharmaceutically acceptable, non-toxic salts, such as acid addition salts. Illustrative of such acid addition salts are hydrochloride, hydrobromide, sulphate, phosphate, fumarate, gluconate, tannate, maleate, acetate, citrate, benzonate, succinate, alginate, pamoate, malate, ascorbate, tartrate, and the like. If the active ingredient is to be administered in tablet form, the tablet may contain a pharmaceutically acceptable diluent which includes a binder, such as tragacanth, corn starch or gelatin; a disintegrating agent, such as alginic acid and a lubricant, such as magnesium stearate.

If administration in liquid form is desired, sweetening and/or flavoring may be used as part of the pharmaceutically-acceptable diluent, and intravenous administration in isotonic saline, phosphate buffer solutions or the like may be effected.

The pharmaceutical compositions will usually contain the peptide in conjunction with a conventional, pharmaceutically-acceptable carrier. Usually, the dosage will be from about 1 to about 100 micrograms of the peptide per kilogram of the body weight of the host when given intravenously; oral dosages will be higher. Overall, treatment of subjects with these peptides is generally carried out in the same manner as the clinical treatment using other antagonists of LHRH.

These peptides can be administered to mammals intravenously, subcutaneously, intramuscularly, orally, intranasally or intravaginally to achieve fertility inhibition and/or control and also in applications calling for reversible suppression of gonadal activity, such as for the management of precocious puberty or during radiation- or chemo-therapy. Effective dosages will vary with the form of administration and the particular species of mammal being treated. An example of one typical dosage form is a physiological saline solution containing the peptide which solution is administered to provide a dose in the range of about 0.1 to 2.5 mg/kg of body weight. Oral administration of the peptide may be given in either solid form or liquid form.

Although the invention has been described with regard to its preferred embodiments, it should be understood that changes and modifications obvious to one having the ordinary skill in his art may be made without departing from the scope of the invention, which is set forth in the claims which are appended thereto. Substitutions known in the art which do not significantly detract from its effectiveness may be employed in the invention.

EXAMPLE I

The synthesis of an analog of the formula:

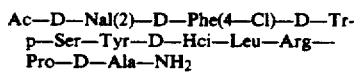

was commenced with the preparation of the intermediate peptide Ac-D-Nal(2)-D-Phe(4-Cl)-D-Trp-Ser-Tyr-D-Lys-Leu-Arg-Pro-D-Ala-$NH_2$. The intermediate peptide was built step by step on a benzhydrylamine resin containing about 0.6 m. equiv. $NH_2/g$ (from BACHEM) on a Beckman 990 synthesizer starting with the Boc-D-Ala in accordance with the procedures set forth below.

Coupling is carried out in accordance with Schedule A as follows:

SCHEDULE A

| Reagent | Mixing Time (mins) |
| --- | --- |
| 1. Boc Amino Acid (0.9-1.2m mole/g. resin) + equiv amt. of DIC | 60-90 |
| 2. MeOH (twice) | 1 |
| 3. $CH_2Cl_2$ (twice) | 1 |

Deblocking is carried out in accordance with Schedule B as follows:

SCHEDULE B

| Reagent | Mixing Time (mins) |
| --- | --- |
| 4. 50% TFA/1% ethanedithiol in $CH_2Cl_2$ (twice) | 15 & 15 |
| 5. IpOH/1% ethane dithiol | 1 |
| 6. 10% TEA in $CH_2Cl_2$ | 2 |
| 7. MeOH | 1 |
| 8. 10% TEA in $CH_2Cl_2$ | 2 |
| 9. MeOH (twice) | 1 & 1 |
| 10. $CH_2Cl_2$ (twice) | 1 & 1 |

Briefly, Boc is used for N-terminal protection. Tos is used fto protect the guanidino group of Arg. Z(2-Cl) is used as the protecting group for the D-Lys side chain, Bzl for the OH group of Ser and Tyr is protected with DCB.

One and a half to two-fold excess of protected amino acid is used based on the $NH_2$-content of the benzhydrylamine-resin, plus one equivalent of DIC in $CH_2Cl_2$ or 10-50% DMF/$CH_2Cl_2$, depending on the solubility of Boc-amino acid, for two hours.

N-Terminal acetylation is performed with a 50-fold excess of acetic anhydride in $CH_2Cl_2$ for 0.5 hours. The protected intermediate peptide thus obtained has the following composition:

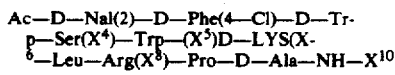

wherein $X^4$ is Bzl and
$X^5$ is DCB, $X^6$ is Z(2-Cl),
$X^8$ is Tos, and
$X^{10}$ is a benzhydryl group incorporated into the resin.

In order to cleave and deprotect the protected peptide-resin, it is treated with 1.4 ml. m-cresole and 15 ml. hydrogen fluoride per gram of peptide-resin for 0.5 hours at 0° and 0.5 hours at room temperature. After elimination of hydrogen fluoride under high vacuum, the resin-peptide is washed with diethyl ether and the peptide is then extracted with DMF and separated from the resin by filtration. The DMF solution is concentrated to a small volume under high vacuum, then triturated with diethyl ether. The crude product thus obtained is purified by preparative HPLC as described below, to give the pure free intermediate peptide having the above-mentioned structure wherein $X^4$, $X^5$, $X^6$, $X^8$ and $X^{10}$ are hydrogen.

The free D-$Lys^6$-containing intermediate peptide is then reacted with potassium cyanate in 80% aqueous DMF solution (81 mg. KCNO/ml), at ambient temperature for 24 hours. The reaction mixture, after evaporation under high vacuum, is subjected to purification by preparative HPLC to yield the desired D-Hci-containing peptide. The peptide is judged to be substantially (95%) pure by using HPLC. HPLC analyses are carried out in a Hewlett-Packard 1090A gradient liquid chromatographic system on a C18 column (VYDAC 218TP546) eluted with solvents A: 0.1% TFA, B: 0.1% TFA in 70% $CH_3CN$ with a gradient of 30–60% in 30 minutes. The intermediate peptide and the desired peptide has a retention times of 25.5 minutes and 28.2 minutes respectively.

Purification of peptides is carried out on a Beckman Prep-350 gradient liquid chromatograph using a 41.4×250 mm preparative reversed phase DYNEMAX C18 cartridge (300A, 12 um) with solvents A: 0.1% TFA and B: 0.1% TFA in 70% $CH_3CN$ and using a gradient of 45–60% in 30 minutes. The pure peptide obtained as TFA salt, if desired, can be converted to the acetate form by passage through an AG3X (Bio-Rad) column in the acetate form followed by lyophilization.

EXAMPLE II

The synthesis of the peptide Ac-D-Nal(2)-D-Phe(4-Cl)-D-Trp-Ser-Tyr-D-Hci(Et)-Leu-Arg-Pro-D-Ala-NH2 accomplished by reacting the the intermediate peptide Ac-D-Nal(2)-Phe(4-Cl)-D-Trp-Ser-Tyr-D-Lys-Leu-Arg-Pro-D-Ala-NH2 described in Example I, with N-ethylisocyanate in DMF (0.1 mg. in 0.01 ml. per gm of intermediate) at 0°-10° for 10 hours. Retention time for the desired peptide is 30.8 min.

EXAMPLE III

The synthesis of the peptide Ac-D-Nal(2)-D-Phe(4-Cl)-D-Trp-Ser-Tyr-D-Cit-Leu-Arg-Pro-D-Ala-NH2 is conducted as described in Example I with the exception that Boc-D-Orn(Z) is incorporated in place of Boc-D-Lys[Z-(2-Cl)] in position 6 of the intermediate peptide to afford another intermediate peptide having the formula Ac-D-Nal(2)-D-Phe (4-Cl)-D-Trp-Ser-Tyr-D-Orn-Leu-Arg-Pro-D-Ala-NH2, which is then similarly converted to the desired peptide. This intermediate peptide and the desired peptide have HPLC retention times of 25.5 min. and 27.8 min., respectively.

EXAMPLE IV

The synthesis of the peptide Ac-D-Nal(2)-D-Phe(4-Cl)-D-Trp-Ser-Tyr-D-Cit(Et)-Leu-Arg-Pro-D-Ala-NH$_2$ is accomplished by reacting the the intermediate peptide Ac-D-Nal(2)-Phe(4-Cl)-D-Trp-Ser-Tyr-D-Orn-Leu-Arg-Pro-D-Ala-NH$_2$ described in Example III, with N-ethylisocyanate in DMF (0.1 mg. in 10 ml. per gm of intermediate) at 0°-10° for 10 hours. Retention time for the desired peptide is 30.4 min.

EXAMPLE V

The synthesis of the peptide Ac-D-Phe(4-Cl)-D-Phe(4-Cl)-D-Trp-Ser-Tyr-D-Hci-Leu-Arg-Pro-D-Ala-NH$_2$ is conducted as described in Example I, with the exception that Boc-D-Phe(4-Cl) is incorporated in place of Boc-D-Nal(2) in position 1 of the intermediate peptide to give another intermediate peptide having ther formula Ac-D-Phe(4-Cl)-D-Phe(4-Cl)-D-Trp-Ser-Tyr-D-Lys-Leu-Arg-Pro-D-Ala-NH$_2$, which in then similarly converted to the desired peptide. This intermediate peptide and the desired peptide have retention times of 24.0 min. and 26.6 min., respectively.

EXAMPLE VI

The synthesis of the peptide Ac-D-Phe(4-Cl)-D-Phe(4-Cl)-D-Trp-Ser-Tyr-D-Hci(Et)-Leu-Arg-Pro-D-Ala-NH$_2$ is accomplished by reacting the the intermediate peptide Ac-D-Phe(4-Cl)-Phe(4-Cl)-D-Trp-Ser-Tyr-D-Lys-Leu-Arg-Pro-D-Ala-NH$_2$ described in Example V with N-ethylisocyanate in DMF (0.1 mg. in 10 ml. per gm of intermediate) at 0°-10° for 10 hours. Retention time for the desired peptide is 29.2 min.

EXAMPLE VII

The synthesis of the peptide Ac-D-Phe(4-Cl)-D-Phe(4-Cl)-D-Trp-Ser-Tyr-D-Cit-Leu-Arg-Pro-D-Ala-NH$_2$ is conducted as described in Example I, with the exception that Boc-D-Phe(4-Cl) is incorporated in place of Boc-D-Nal(2) in position 1 and that Boc-D-Orn(Z) is incorporated in place of Boc-D-Lys[Z(2-Cl)] in position 6 of the intermediate peptide to yield another intermediate peptide having the formula Ac-D-Phe(4-Cl)-D-Phe(4-Cl)-D-Trp-Ser-Tyr-D-Orn-Leu-Arg-Pro-D-Ala-NH$_2$, which is then similarly converted to the desired peptide This intermediate peptide and the desired peptide have retention times of 24.0 min. and 26.3 min., respectively.

EXAMPLE VIII

The synthesis of the peptide Ac-D-Phe(4-Cl)-D-Phe(4-Cl)-D-Trp-Ser-Tyr-D-Cit(Et)-Leu-Arg-Pro-D-Ala-NH$_2$ is accomplished by reacting the intermediate peptide Ac-D-Phe(4-Cl)-D-Phe(4-Cl)-D-Trp-Ser-Tyr-D-Orn-Leu-Arg-Pro-D-Ala-NH$_2$ described in Example VII, with N-ethylisocyanate in DMF$^2$ (0.1 mg. in 10 ml. per gm of intermediate) at 0°-10° for 10 hours. Retention time for the desired peptide is 28.6 min.

EXAMPLE IX

The synthesis of the peptide Ac-D-Nal(2)-D-Phe(4-Cl)-D-Trp-Ser-Tyr-D-Hci-Leu-Arg-Pro-Gly-NH$_2$ is conducted as described in Example I to afford another intermediate peptide having the formula Ac-D-Nal(2)-D-Phe(4-Cl)-D-Trp-Ser-Tyr-D-Lys-Leu-Arg-Pro-Gly-NH$_2$, which is then similarly converted to the desired peptide. This intermediate peptide and the desired peptide have HPLC retention times of 24.8 min. and 27.4 min., respectively.

EXAMPLE X

The synthesis of the peptide Ac-D-Nal(2)-D-Phe(4-Cl)-D-Trp-Ser-Tyr-D-Hci(Et)-Leu-Arg-Pro-Gly-NH$_2$ is accomplished by reacting the the intermediate peptide Ac-D-Nal(2)-Phe(4-Cl)-D-Trp-Ser-Tyr-D-Lys-Leu-Arg-Pro-Gly-NH$_2$ described in Example IX with N-ethylisocyanate in DMF 0.1 mg. in 10 ml. per gm of intermediate) at 0°-10° for 10 hours. Retention time for the desired peptide is 30.0 min.

EXAMPLE XI

The synthesis of the peptide Ac-Pro-D-Phe(4-Cl)-D-Trp-Ser-Tyr-D-Hci-Leu-Arg-Pro-D-Ala-NH$_2$ is conducted as described in Example I with the exception that Boc-Pro is incorporated in place of Boc-D-Nal(2) in position 1 of the intermediate peptide to afford another intermediate peptide having the formula Ac-Pro-D-Phe(4-Cl)-D-Trp-Ser-Tyr-D-Lys-Leu-Arg-Pro-D-Ala-NH$_2$, which is then similarly converted to the desired peptide. This intermediate peptide and the desired peptide have retention times of 16.8 min. and 19.3 min., respectively.

EXAMPLE XII

The synthesis of the peptide Ac-Pro-D-Phe(4-Cl)-D-Trp-Ser-Tyr-D-Hci(Et)-Leu-Arg-Pro-D-Ala-NH$_2$ is accomplished by reacting the the intermediate peptide Ac-D-Pro-Phe(4-Cl)-D-Trp-Ser-Tyr-D-Lys-Leu-Arg-Pro-D-Ala-NH$_2$ described in Example XI, with N-ethylisocyanate in DMF (0.1 mg. in 10 ml. per gm of intermediate) at 0°-10° for 10 hours. Retention time for the desired peptide is 22.0 min.

EXAMPLE XIII

The synthesis of the peptide Ac-Pro-D-Phe(4-Cl)-D-Trp-Ser-Tyr-D-Cit-Leu-Arg-Pro-D-Ala-NH$_2$ is conducted as described in Example I, with the exception that Boc-Pro is incorporated in place of Boc-D-Nal(2) in position 1 and that Boc-D-Orn(Z) is incorporated in place of Boc-D-Lys[Z(2-Cl)] in position 6 of the intermediate peptide to yield another intermediate peptide having the formula Ac-Pro-D-Phe(4-Cl)-D-Trp-Ser-Tyr-D-Orn-Leu-Arg-Pro-D-Ala-NH$_2$. This intermediate peptide and the desired peptide have retention times of 16.85 min. and 18.8 min., respectively.

EXAMPLE XIV

The synthesis of the peptide Ac-Pro-D-Phe(4-Cl)-D-Trp-Ser-Tyr-D-Cit(Et)-Leu-Arg-Pro-D-Ala-NH$_2$ is conducted as described in Example VI, with the exception that the intermediate peptide Ac-Pro-D-Phe(4-Cl)-D-Trp-Ser-Tyr-D-Orn-Leu-Arg-Pro-D-Ala-NH$_2$ described in Example XIII is reacted with N-ethylisocyanate The desired peptide has a retention time of 24.9 min.

EXAMPLE XV

The synthesis of the peptide Ac-D-Phe-D-Phe(4-Cl)-D-Trp-Ser-Tyr-Hci-Leu-Arg-Pro-D-Ala-NH$_2$ is conducted as described in Example I, with the exception that Boc-D-Phe is incorporated in place of Boc-D-Nal(2) in position 1 of the intermediate peptide to yield another intermediate peptide having the formula Ac-D-Phe-Phe(4-Cl)-D-Trp-Ser-Tyr-D-Lys-Leu-Arg-Pro-D-Ala-NH$_2$, which is then similarly converted to the desired peptide This intermediate peptide and the desired peptide have HPLC retention times of 20.8 min. and 23.4 min., respectively.

EXAMPLE XVI

The synthesis of the peptide Ac-D-Phe-D-Phe(4-Cl)-D-Trp-Ser-Tyr-D-Hci(Et)-Leu-Arg-Pro-D-Ala-NH$_2$ is accomplished by reacting the the intermediate peptide Ac-D-Phe-D-Phe(4-Cl)-D-Trp-Ser-Tyr-D-Lys-Leu-Arg-Pro-D-Ala-NH$_2$ described in Example XV, with N-ethylisocyanate in DMF (0.1 mg. in 10 ml. per gm of intermediate) at 0°-10° for 10 hours. Retention time for the desired peptide is 26.0 min.

EXAMPLE XVII

The synthesis of the peptide Ac-D-Phe-D-Phe(4-Cl)-D-Trp-Ser-Tyr-D-Cit-Leu-Arg-Pro-D-Ala-NH$_2$ is conducted as described in Example I, with the exception that Boc-D-Phe is incorporated in place of Boc-D-Nal(2) in position 1 and that Boc-D-Orn(Z) is incorporated in place of Boc-D-Lys[Z(2-Cl)] in position 6 of the intermediate peptide to yield another intermediate peptide having the formula Ac-D-Phe-D-Phe(4-Cl)-D-Trp-Ser-Tyr-D-Orn-Leu-Arg-Pro-D-Ala-NH$_2$. This intermediate peptide and the desired peptide have retention times of 21.0 min. and 23.1 min., respectively.

EXAMPLE XVIII

The synthesis of the peptide Ac-D-Phe-D-Phe(4-Cl)-D-Trp-Ser-Tyr-D-Cit(Et)-Leu-Arg-Pro-D-Ala-NH$_2$ is accomplished by reacting the the intermediate peptide Ac-D-Phe-D-Phe(4-Cl)-D-Trp-Ser-Tyr-D-Orn-Leu-Arg-Pro-D-Ala-NH$_2$ described in Example XVII, with N-ethylisocyanate in DMF (0.1 mg. in 0.01 ml. per gm of intermediate) at 0°-10° for 10 hours. Retention time for the desired peptide is 25.4 min.

EXAMPLE XIX

The synthesis of an analog of the formula:

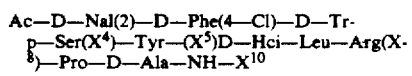

peptide was built step by step on a benzhydrylamine resin containing about 1 0 m. equiv. NH$_2$/g (from BACHEM) on a Beckman 990 synthesizer starting with the Boc-D-Ala in accordance with the procedures set forth below.

Coupling is carried out in accordance with Schedule C as follows:

| SCHEDULE C | |
|---|---|
| Reagent | Mixing Time (mins) |
| 1. Boc Amino Acid (2-3m mole/g. resin) + equiv amt. of DIC | 60-90 |
| 2. MeOH (twice) | 1 |
| 3. CH$_2$Cl$_2$ (twice) | 1 |

Deblocking is carried out in accordance with Schedule B as follows:

| SCHEDULE D | |
|---|---|
| Reagent | Mixing Time (mins) |
| 4. 50% TFA/1% ethanedithiol in CH$_2$Cl$_2$ (twice) | 15 & 15 |
| 5. IpOH/1% ethane dithiol | 1 |
| 6. 10% TEA in CH$_2$Cl$_2$ | 2 |
| 7. MeOH | 1 |
| 8. 10% TEA in CH$_2$Cl$_2$ | 2 |
| 9. MeOH (twice) | 1 & 1 |
| 10. CH$_2$Cl$_2$ (twice) | 1 & 1 |

Briefly, Boc is used for the protection of the alpha-amino groups. Tos is used to protect the quanidino group of Arg. DCB is used as the protecting group for the phenolic hydroxyl group of Tyr, and the OH group of Ser is protected with Bzl. Two to three-fold excess of protected amino acid is used based on the NH$_2$-content of the benzhydryl-amine-resin, plus one equivalent of DIC in CH$_2$Cl$_2$ or 10-50% DMF/CH$_2$Cl$_2$, depending on the solubility of Boc-amino acid, for two hours.

N-Terminal acetylation is performed with a 50-fold excess of acetic anhydride in CH$_2$Cl$_2$ for 0.5 hours. The protected intermediate peptide thus obtained has the following composition:

Ac—D—Nal(2)—D—Phe(4—Cl)—D—Tr-p—Ser(X$^4$)—Tyr—(X$^5$)D—Hci—Leu—Arg(X$^8$)—Pro—D—Ala—NH—X$^{10}$ wherein
X$^4$ is Bzl and
X$^5$ is DCB,
X$^8$ is Tos, and X$^{10}$ is a benzhydryl group incorporated into the resin.

In order to cleave and deprotect the protected peptide-resin, it is treated with 1.4 ml. m-cresole and 15 ml. hydrogen fluoride per gram of peptide-resin for 0.5 hours at 0° and 0.5 hours at room temperature. After elimination of hydrogen fluoride under high vacuum, the resin-peptide is washed with diethyl ether and the peptide is then extracted with DMF and separated from the resin by filtration. The DMF solution is concentrated to a small volume under high vacuum, then triturated with diethyl ether. The crude product thus obtained is purified by preparative HPLC as described below to yield the desired D-Hci-containing peptide. The peptide is judged to be substantially (95%) pure by using HPLC. HPLC analyses are carried out in a Hewlett-Packard 1090A gradient liquid chromatographic system on a "PHENOMENEX" (W-Porex 5C18) column, eluted with solvents A: 0.1% TFA, B: 0.1% TFA in 70% CH$_3$CN with a gradient of 35-75% in 30 minutes. The desired peptide has retention time of 22.9 minutes.

Purification of peptides is carried out on a Beckman Prep-350 gradient liquid chromatograph using a 41.4×250 mm preparative reversed phase DYNAMAX C18 cartridge (300A, 12 um) with solvents A: 0.1% TFA and B: 0.1% TFA in 70% CH$_3$CN and using a gradient of 45-60% in 30 minutes. The pure peptide obtained as TFA salt, if desired, can be converted to the acetate form by passage through an AG3X (Bio-Rad) column in the acetate form followed by lyophilization.

EXAMPLE XX

The synthesis of the peptide H$_2$N-CO-D-Nal(2)-D-Phe(4Cl)-D-Trp-Ser-Tyr-D-Hci-Leu-Arg-Pro-D-Ala- NH$_2$ is conducted as described in Example XIX, with the exception that H$_2$N-CO-D-Nal(2) is incorporated in place of Boc-D-Nal(2) in position 1, and the N-terminal acetylation is omitted to yield the desired peptide with retention time of 24.0 min.

EXAMPLE XXI

The synthesis of the peptide Ac-D-Nal(2)-D-Phe(4-Cl)-D-Trp-Ser-Tyr-D-Cit-Leu-Arg-Pro-D-Ala-NH$_2$ is conducted as described in Example XIX, with the exception that Boc-D-Cit is incorporated in place of Boc-D-Hci in position 6 to give the desired peptide with a retention time of 22.5 min.

EXAMPLE XXII

The synthesis of the peptide Ac-D-Phe(4-Cl)-D-Phe(4-Cl)-D-Trp-Ser-Tyr-D-Hci-Leu-Arg-Pro-D-Ala-NH$_2$ is conducted as described in Example XIX with the exception that BOC-D-Phe(4-Cl) is incorporated in place of Boc-D-Nal(2) in position 1 to give the desired peptide with a retention time of 24.0 min.

EXAMPLE XXIII

The synthesis of the peptide Ac-D-Phe(4-Cl)-D-Phe(4-Cl)-D-Trp-Ser-Tyr-D-Cit-Leu-Arg-Pro-D-Ala-NH$_2$ is conducted as described in Example XIX, with the exception that Boc-D-Phe(4-Cl) is incorporated in place of Boc-D-Nal(2) in position 1 and that Boc-D-Cit is incorporated in place of Boc-D-Hci in position 6 to yield the desired peptide having a HPLC retention time of 20.8 min.

EXAMPLE XXIV

The synthesis of the peptide Ac-D-Nal(2)-D-Phe(4-Cl)-D-Trp-Ser-Tyr-D-Hci-Leu-Arg-Pro-Gly-NH$_2$ is conducted as described in Example XIX, with the exception that Boc-Gly is incorporated in place of Boc-D-Ala in position 10. The desired peptide thus obtained has a HPLC retention time of 22.4 min.

EXAMPLE XXV

The synthesis of the peptide Ac-D-Nal(2)-D-Phe(4-Cl)-D-Pal(3)-Ser-Tyr-D-Hci-Leu-Arg-Pro-D-Ala-NH$_2$ is conducted as described in Example XIX with the exception that Boc-D-Pal(3) is incorporated in place of Boc-D-Trp in position 3. The desired peptide has an HPLC retention time of 13.6 min.

EXAMPLE XXVI

The synthesis of the peptide Ac-D-Nal-D-Phe(4-Cl)-D-Pal(3)-Ser-Tyr-D-Cit-Leu-Arg-Pro-D-AlaNH$_2$ is conducted as described in Example XIX, with the exception that Boc-D-Cit is incorporated in place of D-Hci in position 6 and that Boc-D-Pal(3) is incorporated in place of Boc-D-Trp in position 3. The desired peptide has an HPLC retention time of 13.3 min.

EXAMPLE XXVII

The synthesis of the peptide H N-CO-D-Nal(2)-D-Phe(4-Cl)-D-Pal(3)-Ser-Tyr-D-Cit-Leu-Arg-Pro-D-Ala-NH$_2$ is conducted as described in Example XIX, with the exception that Boc-D-Cit is incorporated in place of Boc-D-Hci in position 6, that Boc-D-Pal(3) is incorporated in place of Boc-D-Trp in position 3, and that N-terminal acetylation is omitted to yield the intermediate peptide H-D-Nal(2)-D-Phe(4-Cl)-D-Pal(3)-Ser-Tyr-D-Cit-Leu-Arg-Pro-D-Ala-NH$_2$. The free peptide thus obtained is then reacted with potassium cyanate in 80% aqueous DMF (81 mg. KOCN/300 mg. peptide/ml.) at ambient temperature for 24 hours. The reaction mixture, after evaporation under high vacuum, is subjected to purification by preparative HPLC to yield the desired peptide having HPLC retention time of 14.4 min.

EXAMPLE XXVIII

The synthesis of the peptide H N-CO-D-Nal(2)-D-Phe(4-Cl)-D-Pal(3)-Ser-Tyr-D-Hci-Leu-Arg-Pro-D-Ala-NH$_2$ is conducted as described in Example XIX, with the exception that Boc-D-Pal(3) is incorporated in place of Boc-D-Trp in position 3 and that N-terminal acetylation is omitted to yield the intermediate peptide H-D-Nal(2)-D-Phe(4-Cl)-D-Pal(3)-Ser-Tyr-D-Hci-Leu-Arg-Pro-D-Ala-NH$_2$. The free peptide thus obtained is then reacted with potassium cyanate in aqueous DMF (81 mg. KOCN/300 mg. peptide/ml.) at ambient temperature for 24 hours. The reaction mixture, after evaporation under high vacuum, is subjected to purification by preparative HPLC to give the desired peptide having a HPLC retention time of 14.7 min.

EXAMPLE XXIX

The synthesis of the peptide H N-CO-D-Nal(2)-D-Phe(4-Cl)-D-Trp-Ser-Tyr-D-Cit-Leu-Arg-Pro-D-Ala-NH$_2$ is commenced with the preparation of intermediate peptide H-D-Nal(2)-D-Phe(4-Cl)-D-Trp-Ser-Tyr-D-Cit-Leu-Arg-Pro-D-Ala-NH$_2$. The synthesis of the intermediate peptide is accomplished as described in Example XIX, with the exception that Boc-D-Orn(Z) is incorporated in place of Boc-D-Hci in position 6 and that N-terminal acetylation is omitted The free D-Orn$^6$-containing peptide is then reacted with potassium cyanate in 80% aqueous DMF (162 mg. KPCN/300 mg. peptide/ml.) at ambient temperature for 24 hours. The reaction mixture, after evaporation under high vacuum, is subjected to purification by preparative HPLC to yield the desired peptide with a HPLC retention time of 23.6 min.

EXAMPLE XXX

The synthesis of the peptide H$_2$N-CO-D-Nal(2)-D-Phe(4-Cl)-D-Trp-Ser-Tyr-D-Hci-Leu-Arg-Pro-D-Ala-NH$_2$ is commenced with the preparation of intermediate peptide H-D-Nal(2)-D-Phe(4-Cl)-D-Trp-Ser-Tyr-D-Lys-Leu-Arg-Pro-D-Ala-NH$_2$. The synthesis of the intermediate peptide is accomplished as described in Example XIX, with the exception that Boc-D-Lys[Z(2-Cl)] is incorporated in place of Boc-D-Hci in position 6 and that N-terminal acetylation is omitted. The free D-Lys$^6$-containing peptide is then reacted with potassium cyanate in 80% aqueous DMF *164 mg. KOCN/300 mg. peptide/ml.) at ambient temperature for 24 hours. The reaction mixture, after evaporation under high vacuum, is subjected to purification by preparative HPLC to yield the desired peptide with a HPLC retention time of 24.0 min.

EXAMPLE XXXI

Tablet formulation for buccal (e.g., sublingual) administration:
1. LHRH Antagonist 10.0 mg. Compressible Sugar, USP 86.0 mg. Calcium Stearate 4.0 mg.
2. LHRH Antagonist 10.0 mg. Compressible Sugar, USP 88.5 mg. Magnesium Stearate 1 5 mg.
3. LHRH Antagonist 5.0 mg. Mannitol, USP 83.5 mg. Magnesium Starch, USP 1.5 mg.

4. LHRH Antagonist 10.0 mg. Pregelatinized Starch, USP 10.0 mg. Lactose, USP 74.5 mg. Pregelatinized Starch, USP 15.0 mg. Magnesium Stearate, USP 1.5 mg.

Method A. LHRH Antagonist is dissolved in a sufficient quantity of water to form a wet granulation when mixed with the sugar portion of the excipients. After complete mixing the granulation is dried in a tray of fluid-bed dryer. The dry granulation is then screened to break up any large aggregates and then mixed with the remaining components. The granulation is then compressed on a standard tableting machine to the specific tablet weight.

Method B. In this manufacturing method, all formulations would include 0.01% gelatin, USP. The gelatin would be first dissolved in the aqueous granulation solvent followed by the LHRH analog. The remaining steps are as in (a) above.

EXAMPLE XXXII

Long Acting Intramuscular Injectable Formulation

Long Acting iM. Injectable—Sesame Oil Gel LHRH Antagonist 10.0 mg. Aluminum Monostearate, USP 20.0 mg. Sesame oil g.s. ad 1.0 ml.

The aluminum monostearate is combined with the sesame oil and heated to 125° C. with stirring until a clear yellow solution forms. This mixture is then autoclaved for sterility and allowed to cool. The LHRH antagonist is then added aseptically with trituration. Particularly preferred LHRH antagonists are salts of low solubility, e.g., zinc salts, zinc tannate salts, pamoate salts, and the like. These exhibit exceptionally long duration of activity.

EXAMPLE XXXIII

Long Acting IM Injectable—Biodegradable Polymer Microcapsules

LHRH Antagonists 1% 25/75 glycolide/lactide copolymer (0.5 intrinsic viscosity) 99%
Microcapsules (0°-150°) of above formulation suspended in:
Dextrose 5.0% CMC, sodium 0.5% Benzyl alcohol 0.9% Tween 80 0.1% Water, purified q.s. 100.0% 25 mg. of microcapsules are suspended in 1.0 ml. of vehicle.

EXAMPLE XXXIV

Aqueous Solution for Intramuscular Injection

LHRH Antagonist 500 mg. Gelatin, nonantigenic 5 mg. Water for injection g.s. ad 100 ml.

The gelatin and LHRH antagonist are dissolved in water for injection, then the solution is sterile filtered.

EXAMPLE XXXV

Formulation for Rectal Administration

Suppository Vehicle for Rectal Administration

LHRH Antagonist 5 0 mg. Witepsol H15 20.0 mg.

The LHRH antagonist is combined with the molten Witepsol H15, mixed with and poured into 2 gm. molds.

We claim:

1. A peptide having the formula:

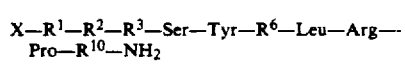

wherein
X is acetyl,
$R^1$ is D-Nal(2),
$R^2$ is D-Phe(4Cl),
$R^3$ is D-Trp or D-Pal(3),
$R^6$ is D-Cit or D-Hci, and
$R^{10}$ is D-Ala
and the pharmaceutically acceptable acid addition salts thereof.

2. A peptide of claim 1 wherein $R^3$ is D-Pal(3).

* * * * *

UNITED STATES PATENT AND TRADEMARK OFFICE
CERTIFICATE OF CORRECTION

PATENT NO. : 5,198,533
DATED : March 30, 1993
INVENTOR(S) : Schally, et al

It is certified that error appears in the above-indentified patent and that said Letters Patent is hereby corrected as shown below:

On the title page, under [56] Other Publications, second column, line 7, delete "Sntagonists", insert --Antagonists--.

line 9, delete "Blomed Research Chemical", insert --Zeitschrift fur Naturforschung, vol 42b, 101-107 (1987)--; and line 10, preceding "Abstract", insert --Chemical--.

Signed and Sealed this

Twentieth Day of August, 1996

*Attest:*

BRUCE LEHMAN

*Attesting Officer*        *Commissioner of Patents and Trademarks*